United States Patent [19]

Kaiser

[11] Patent Number: Plant 5,337

[45] Date of Patent: Nov. 13, 1984

[54] DISTINCT VARIETY OF STREPTOCARPUS NAMED REVOLTE

[75] Inventor: Herbert Kaiser, Rieskirchen, Fed. Rep. of Germany

[73] Assignee: Oglevee Associates, Inc., Connellsville, Pa.

[21] Appl. No.: 494,550

[22] Filed: May 13, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus plant is characterized by its small, narrow and flattened leaves. The plant has bouquet-type flowers standing above the leaf line. The flowers have a flattened appearance due to the flat bottom petals and reflexed top petals.

1 Drawing Figure

BACKGROUND OF THE NEW PLANT

The present invention comprises a new and distinct cultivar of Streptocarpus × hybridus known by the varietal name of Revolte. The new cultivar is the product of a selective breeding program and is a hybridization of English hybrids of which the standard was a Streptocarpus known by the varietal name Kolibri. The new cultivar differs from the English hybrids in respect of color, early flowering, plant form and growth characteristics.

The new cultivar is generally characterized by its small, narrow and flattened leaves. The plant has bouquet-type flowers standing above the leaf line. The flowers have a flattened appearance resulting from flat bottom petals and reflexed top petals.

The new cultivar was discovered in 1979 in Reiskirchen, Federal Republic of Germany; was first asexually reproduced by cuttings in Reiskirchen, Federal Republic of Germany; and has been repeatedly asexually reproduced by cuttings at Oglevee Floral Company in Connelsville, Pa. It has been found to retain its distinctive characteristics through successive propagations.

The new cultivar, when grown in a greenhouse in Connellsville, Pa., has a response time of eight weeks from a well-rooted young plant in a 2¼ inch pot to a flowering plant in a 6 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out by the Oglevee Floral Company in Connellsville, Pa. The plant history was taken on eight week plants blossomed under natural light in a greenhouse and color readings were taken indoors under 100 foot candles of cool white fluorescent light. Color references are to the R.H.S. Colour Chart of The Royal Horticultural Society of London unless noted differently.

Botanical classification: Gesneriaceae (Family); *Streptocarpus* × *hybridus* (Genus × species).

Flower:

*Fully expanded.*—4.5 To 5 centimeters.

*Borne.*—In clusters of two to six flowers per flower stalk above the foliage. Flower stalk arises from mid-rib of each leaf.

*Stem.*—Single, long, pubescent and round.

*Form.*—Funnel formed in an umbel with upper two petals reflexed and lower petals flattened to give overall flat appearance.

*Permanence.*—Long lasting 21 to 25 days.

Color:

*Tonality from a distance.*—Rose Pink 37 with purple 39 splotch and dark veining (Exotica III).

*Front of petals.*—Fan 2 Red Purple Group 73A.

*Base of petals.*—Splotch of Fan 2 Red Purple Group 74B with the bottom three petals having veining Fan 2 Red Purple Group 72B.

*Reverse of petals.*—Fan 2 Red Purple Group 75C.

*Discoloration.*—Insignificant.

Petals:

*Texture.*—Flat.

*Appearance.*—Individually lobed with slightly cuneate margins; top two petals reflexed and bottom three petals flat.

*Arrangement.*—Regularly united into an elliptical form.

*Persistence.*—21 To 25 days and remains on plant in dry form until picked.

*Fragrance.*—None.

Reproductive organs:

*Anthers.*—Nonexistent.

*Filament.*—Attached to petals and terminate in small, undeveloped tips about 2 to 3 centimeters up from base.

*Pollen.*—Nonfertile.

*Pistil.*—2 To 2.5 centimeters long.

*Style.*—White, 0.5 to 0.6 centimeter with greenish base.

*Stigma.*—White, flattened and T-shaped.

*Ovaries.*—1.5 Centimeters and purple.

Plant:

*Form.*—Leaves rosette from a crown at the soil line.

*Growth.*—A spreading, free flowing habit with leaves being elliptical.

*Height from soil line.*—7 To 10 centimeters.
*Spread.*—30 To 40 centimeters.

Foliage:

*Size.*—10 To 27 centimeters long and 3 to 6 centimeters wide at widest point.
*Quantity.*—12 To 20 leaves.
*Shape.*—Elliptical.
*Top side.*—Fan 3 Green Group 137A.
*Under side.*—Fan 3 Green Group 138D.

*Ribs and veins.*—Pinnate.
*Rib and vein color.*—Fan 3 Green Group 145C.
*Margin.*—Cuneate.
*Leaf tips.*—Obtuse.
*Leaf base.*—Acute.

I claim:

1. A new and distinct variety of Streptocarpus substantially as herein shown and described.

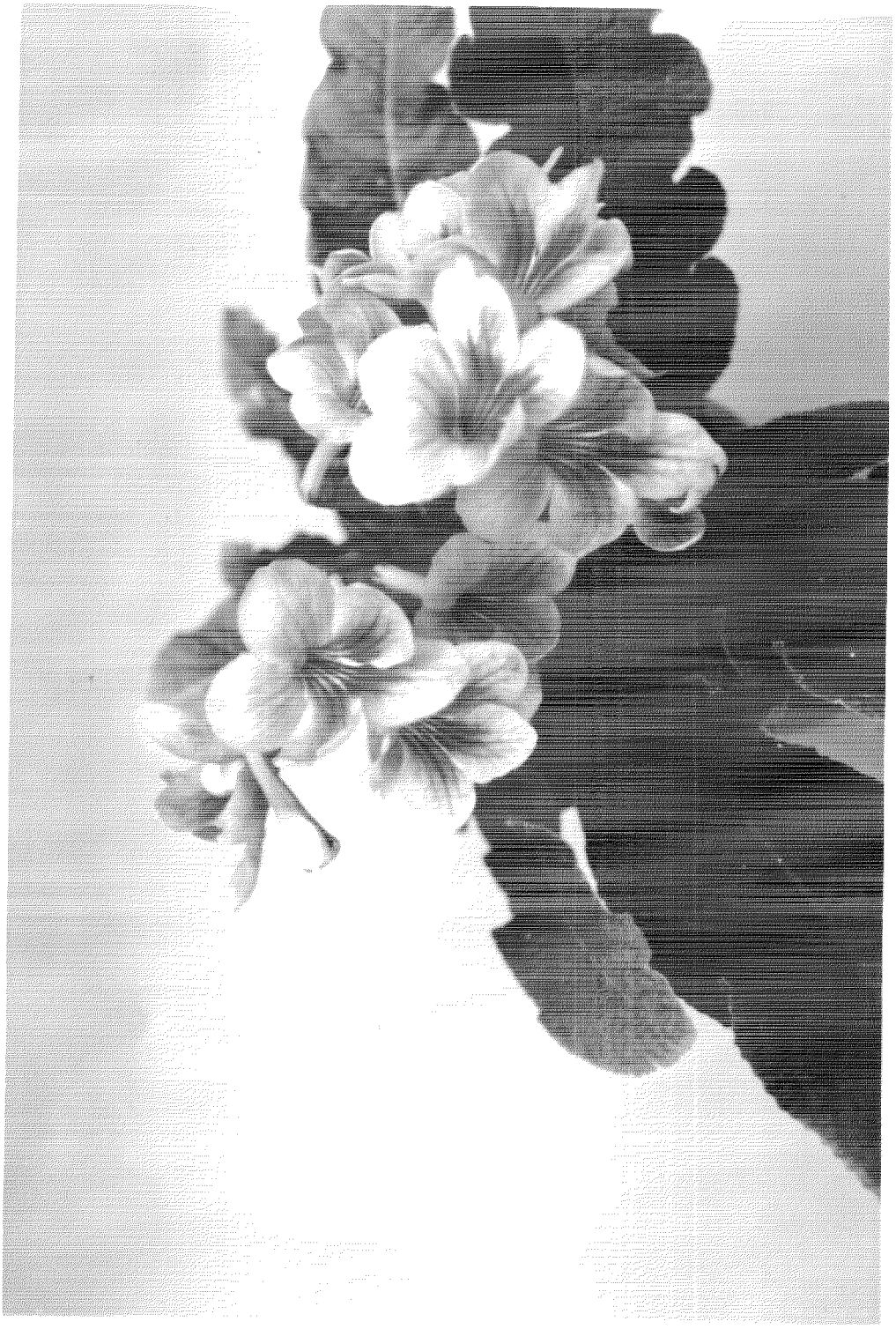

* * * * *